United States Patent [19]

Orejola

[11] Patent Number: 5,779,727
[45] Date of Patent: Jul. 14, 1998

[54] HYDRAULICALLY OPERATED SURGICAL SCISSORS

[76] Inventor: Wilmo C. Orejola, 144 Mountain Ave., Pompton Plains, N.J. 07444-1020

[21] Appl. No.: 802,780

[22] Filed: Feb. 18, 1997

[51] Int. Cl.$^6$ ............................................. A61B 17/32
[52] U.S. Cl. ................................................. 606/174
[58] Field of Search ........................... 606/174, 205, 606/170; 30/194, 211, 187, 191, 193

[56] References Cited

U.S. PATENT DOCUMENTS 5,254,130  10/1993  Poncet et al. .................. 606/174 X
5,361,503  11/1994  Huitema .......................... 606/205 X

*Primary Examiner*—Michael H. Thaler
*Attorney, Agent, or Firm*—Linval B. Castle

[57] ABSTRACT

A highly maneuverable surgical scissors at the end of an 8 mm. diameter flexible arm 45 cm. in length and controlable by a scissors handle at the opposite end is designed for modern thoracoscopic and laparoscopic surgery through a "button-hole" access port in a minimally invasive procedure.

6 Claims, 3 Drawing Sheets

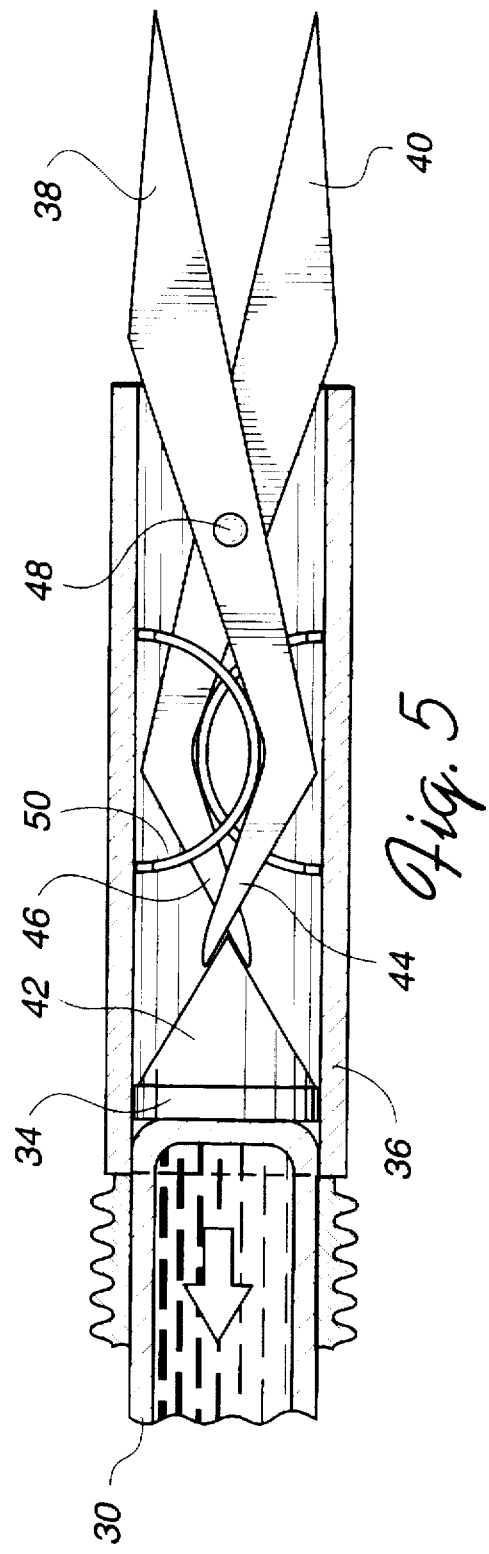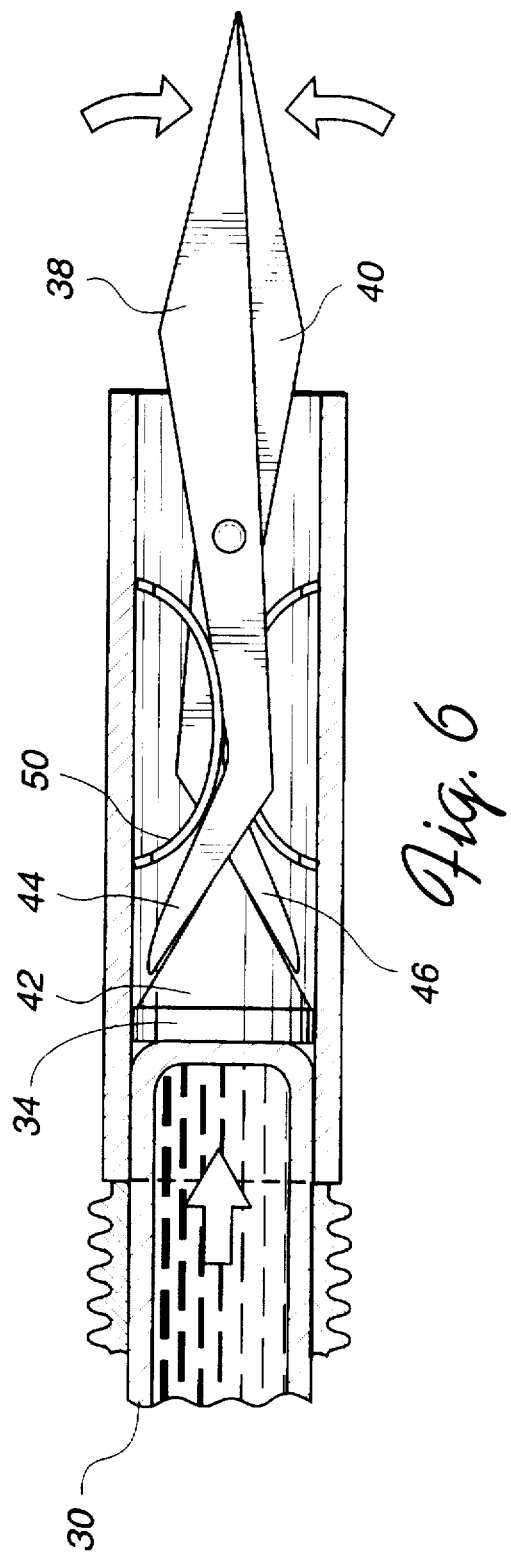

HYDRAULICALLY OPERATED SURGICAL SCISSORS

This invention relates to surgical instruments and in particular to a very small and maneuverable surgical scissors that can be manipulated deep inside the body of a patient from a position outside the body.

BACKGROUND OF THE INVENTION

The constraint of high medical costs has spurned the impetus to adopt less invasive and more innovative procedures as more practical alternatives to expensive medical procedures. A minimally invasive procedure cuts across the time and cost of morbidities and hospitalization attendant to more standard surgical approaches. And with the use of video imaging minimally invasive procedures have been successfully achieved even in major operations in abdominal and thoracic surgery.

As a new emerging technology, video assisted thoracoscopic or laparoscopic surgery has certain difficulties to overcome. One of the most interesting parts of this innovative approach in surgery is the ability of the surgeon to operate on a wide scope inside the chest or abdomen through a button-hole access port. These ports serve as access for deep surgical instrumentation and, of course, for the videoscope for visualization.

At the present time the thoroscopic devices available are rigid and offer little room for rotation, angulation or reverse manipulation. In laparoscopic surgery, the softness of the abdominal wall may yield a certain degree of maneuvers through button-hole access ports. Peculiar to thoroscopic operation, however, the rib cage limits this degree of freedom in laparoscopic surgery. The ribs and costal cartilages being firm and fixed oppose any torque or rotating motions and require additional ports for directional maneuvers. Rigid instruments become more difficult to manipulate. While rotational, reverse and other angular directions of motions are paramount in surgical technique of cutting, sewing and tying deep structures inside the chest, good outcome of surgery may not have to be compromised. When called for, flexible instruments will make surgical instrumentation more manageable.

This invention is for a surgical scissors that is flexible and completely maneuverable through a button-hole access port.

Briefly described, the invention is for a surgical scissors that is designed for deep instrumentation in thoracocopic and laparoscopic surgeries. The scissors is attached to the end of a sealed hydraulic tube and may be removed and replaced with other instruments for cutting, sewing, tying or deep tissue retracting. When attached to the flexible tube, the scissors is widely maneuverable inside a chest or abdominal cavity through button-hole access ports in a minimally invasive procedure. dr

DESCRIPTION OF THE DRAWINGS

In the drawings which illustrate the preferred embodiment of the invention:

FIG. 5 is a sectional view of the scissors in an open position; and

FIG. 6 is a sectional view of the scissors in a closed position.

DETAILED DESCRIPTION OF THE PREFERRED EMBODIMENT

The invention is for a surgical instrument that is specially designed for deep instrumentation in thoracoscopic and laparoscopic surgeries through button-hole access ports and with the aid of video imaging. Its flexibility makes it easy to maneuver in a wide range of rotation, angulation or reverse motion inside a chest or abdominal cavity in a minimally invasive procedure. The scissors assembly may also be removed and replaced with various instruments for cutting, sewing, tying, or deep tissue retracting.

Figure 1:
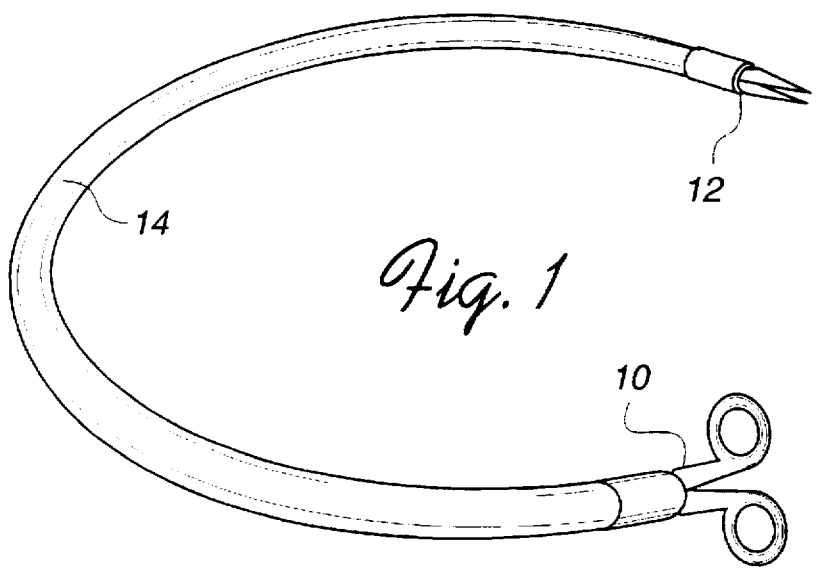
FIG. 1 is a perspective view of the surgical instrument.

The surgical instrument may be made of metal or plastic material and , as shown in FIG. 1, constitutes three major components: the manipulator 10 which resembles a scissors handle, the and the tubular flexible arm 14 which is coupled between the manipulator 10 and the operator 12 and hydraulically transmits the cutting motions of the manipulator to the operator. Each of these major components can be assembled and disassembled for cleaning, sterilization, repair and replacement, if not made disposable. The operator 12 may be screwed into the end of the flexible arm 14 and may be replaced with other operator components of intended use.

Figure 2:
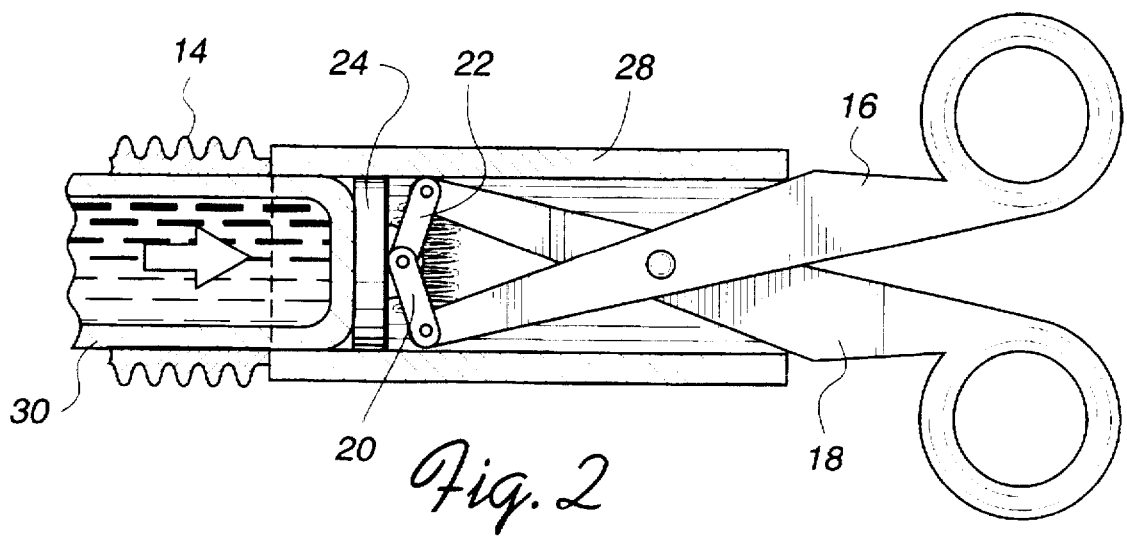
FIG. 2 is a sectional view of the manipulator in an open position.
Figure 3:
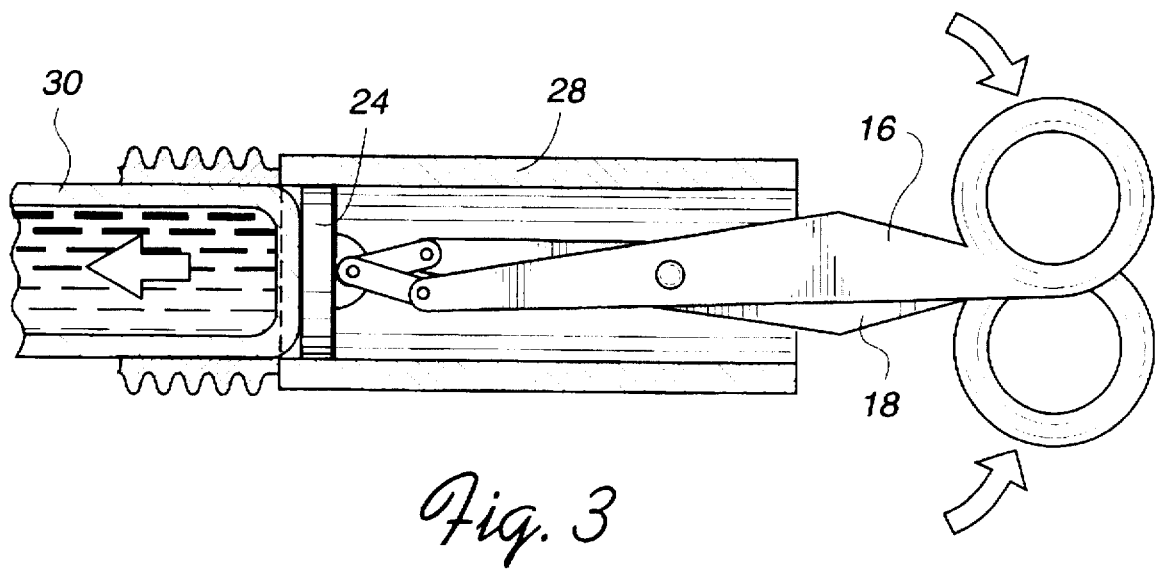
FIG. 3 is a sectional view of the manipulator in a closed position.

The manipulator 10, shown in detail in FIGS. 2 and 3, is comprised of a pair of levers 16, 18 that are pivoted together near their centers at fulcrum 21. Levers 16, 18 each have ring handles for a thumb and index finger at one end and the opposite ends are pivotally coupled to the first ends of piston rods 20, 22, the second ends of which are pivotally coupled together and to the center of a cup shaped piston 24. A spring 26 is connected to the first ends of the piston rods 20, 22 to keep the ring handles of the levers 16, 18 normally spread apart.

The piston 24 has a diameter that enables it to slide freely within the tubular member 28 so that its end surface will contact the sealed flexible tube 30 in the flexible arm 14. The flexible tube 30 is a soft waterproof rubber sheath filled with its entire length water or saline that is moved by the action of the piston 24 to transmit the piston force to the opposite end of the flexible arm.

FIG. 3 illustrates the mechanical action of the manipulator from its position in FIG. 2. In FIG. 3, the ring handles of the manipulator have been closed to force the piston 24 to move in the tubular member 28 against the end of the liquid filled rubber tube 30 in the flexible arm 14. This will transmit energy through the flexible arm to the operator 12 at the opposite end of the arm.

Figure 4:
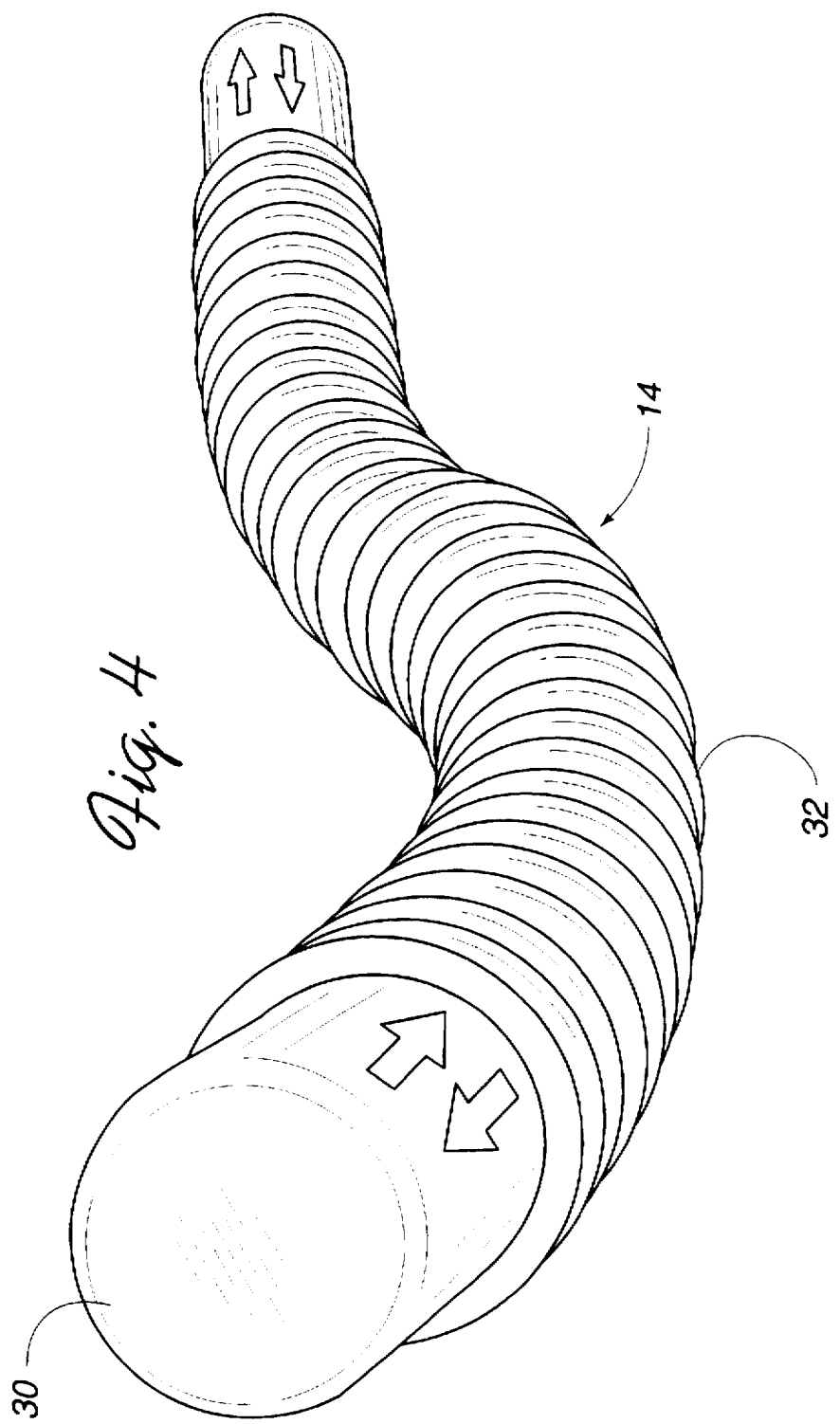
FIG. 4 is an enlarged perspective view of the flexible arm.

FIG. 4 is a perspective view of the tubular flexible arm 14 showing the moveable and sealed soft rubber sheath 30 at the ends. The flexible arm 14 is protected by a metal or plastic coil 32 which FIG. 4 is a perspective view of the tubular flexible arm 14 showing the moveable and sealed soft rubber sheath 30 at the ends. The flexible arm 14 is protected by a metal or plastic coil 32 which enables the arm to flex or twist to sharp angles without kinking and remain so until readjusted. While the flexible arm 14 may be made of different sizes and lengths, an overall length of 45 cm. and a diameter of 8 mm. may be considered standard. The flexible arm if firmly secured to the manipulator by a screw attachment which permits the removable of the individual parts for cleaning and sterilization.

The closing of the levers 16, 18 of the manipulator 10 moves the piston 24 against the end of the soft rubber tube 30 in the flexible arm 14, as shown in FIG. 3. This exerts a corresponding force against the first side of a piston 34 in the operator 12 located at the end of the flexible arm opposite the manipulator. The piston 34 slides freely within a tubular member 36 and functions to open and close the cutting blades 38, 40 of a surgical scissors, as shown in FIG. 5. The operator assembly which includes the surgical scissors may be removed from the flexible arm for cleaning, or it may be replaced by other operators such as graspers or other necessary fixtures.

The first side of the piston 34 is contacted by the soft rubber hydraulic tube 30 in the flexible arm 12. The second side of piston 34 is a cone 42 with its apex on the centerline of the piston and pointed from the piston. The cone 42 functions to close the blades 38, 40 of the scissors by forcing apart the blade extensions 44, 46.

The blades 38, 40 of the surgical scissors are pivoted together near their centers at the fulcrum 48 and extend back in the tubular member 36 where they are tapered and bent in an obtuse angle to form free ends or blade extensions 44, 46. The ends of the blade extensions slightly overlap and are held in this position by the apex of cone 42 while the cone and piston 34 are in a relaxed position as shown by the arrow of FIG. 5. In this position, the blades 39, 40 are open and semi-circular springs 50, between the interior wall of the tubular member 36 and the blades at their obtuse angle bend, urge the blades to remain in this open position.

As the handles 16,18 of the manipulator 10 are closed, the piston 24 of the manipulator moves against the hydraulic tube 30 in the flexible arm 12, and the tube exerts a force against the first side of the piston 34 in the operator 12, or scissors assembly. The piston and its cone 42 are therefore moved so that the cone forces apart the blade extensions 44 and 46 to close the blades 38,40, as shown in FIG. 6.

As the handles 16,18 of the manipulator 10 are opened, the force applied to the piston 34 is relaxed so that the semi-circular springs 50 in the scissors assembly can again open the blaces 38,40 and reset the piston 34 and cone 42 to the position shown in FIG. 5. The hydraulic scissors thus functions as an ordinary scissors so that when the manipulator is closed, the operator assembly blades close. The additional feature of the hydraulic scissors is the ability to bend the flexible arm reverse or to any angulation desired while making a cut.

I claim:

1. A hydraulically operated surgical scissors comprising:
    a tubular flexible arm containing over its length a sealed pliable tube filled with fluid, said flexible arm having a first and a second end;
    a manipulator attached to the first end of said flexible arm, said manipulator including a tubular member aligned with said flexible arm and containing a slideable piston having first and second surfaces, said first surface in communication with said sealed pliable tube for exerting a force against said tube, said manipulator including a pair of normally open, elongated scissor handles with thumb and index finger rings protruding from an open end of said tubular member, said handles being pivoted together near the center of their lengths, each handle of said pair being pivotally coupled to a corresponding short link which is pivotally coupled to said second surface of said piston whereby closure of said finger rings forces said piston against said pliable tube; and
    an operator removably attached to the second end of said flexible arm, said operator including a scissors having a pair of blades having first and second ends, said blades being closed by the movement of an operator piston in contact with said sealed pliable tube.

2. The surgical scissors claimed in claim 1 wherein said operator includes a spring associated with said scissors for returning said scissors to an open position upon the removal of force on said pliable tube by said manipulator.

3. The surgical scissors claimed in claim 2 wherein said blades of said scissors are normally held open by said spring and are closed by a force against said operator piston by said pliable tube.

4. The surgical scissors claimed in claim 1 wherein said operator includes a tubular housing aligned with the second end of said flexible arm, said operator piston being in a first end of said housing joining said flexible arm, the first end of said scissors blades protruding from a second end of said housing.

5. The surgical scissors claimed in claim 4 wherein said operator includes:
    the pair of scissor blades, said pair of blades being pivoted together at the approximate center of their lengths, said second ends of said pair of blades being bent in an obtuse angle whereby the second end of one of said blades will overlap the second end of the other one of said blades;
    a cone formed on the surface of said operator piston opposite said pliable tube, said cone having its apex between the overlapped second ends of said blades for separating said second ends and for closing said first ends upon an application of force on said operator piston by said pliable tube; and
    spring means between an inner wall of said tubular housing and said blades for opening said first ends upon removal of said force.

6. The surgical scissors claimed in claim 1 wherein said scissor handles of said manipulator are urged into their normally open state by spring means.

* * * * *